(12) United States Patent
Arakawa et al.

(10) Patent No.: US 8,036,338 B2
(45) Date of Patent: Oct. 11, 2011

(54) METHOD AND DEVICE FOR SIMULTANEOUS MEASUREMENT OF MAGNETOSTRICTION AND MAGNETIZATION

(75) Inventors: Etsuo Arakawa, Higashimurayama (JP); Noriyuki Aizawa, Kodaira (JP); Koichi Maruyama, Okazaki (JP)

(73) Assignees: Tokyo Gakugei University, Tokyo (JP); National Institutes of Natural Sciences, Tokyo (JP)

( * ) Notice: Subject to any disclaimer, the term of this patent is extended or adjusted under 35 U.S.C. 154(b) by 375 days.

(21) Appl. No.: 11/887,265

(22) PCT Filed: Nov. 24, 2005

(86) PCT No.: PCT/JP2005/021586
§ 371 (c)(1),
(2), (4) Date: Jul. 24, 2009

(87) PCT Pub. No.: WO2006/120775
PCT Pub. Date: Nov. 16, 2006

(65) Prior Publication Data
US 2010/0013469 A1 Jan. 21, 2010

(30) Foreign Application Priority Data
Mar. 28, 2005 (JP) ................................ 2005-093200

(51) Int. Cl.
*G01N 23/20* (2006.01)
(52) U.S. Cl. .......................................... 378/71; 378/70
(58) Field of Classification Search .................... 378/70, 378/71, 79–83, 86–90; 367/156, 158
See application file for complete search history.

(56) References Cited

U.S. PATENT DOCUMENTS

2003/0221750 A1* 12/2003 Pecharsky et al. ............. 148/121
2004/0021397 A1* 2/2004 Srinivasan ..................... 310/311

FOREIGN PATENT DOCUMENTS

| JP | A-57-044868 | 3/1982 |
| JP | B2-2771433 | 4/1998 |
| JP | B2-3332125 | 7/2002 |

(Continued)

OTHER PUBLICATIONS

Birss et al., "A Capacitive Instrument for the Measurement of a Large Range of Magnetostriction at Low Temperatures and High Fields", 1978, Journal of Physics E:Scientific Instruments, vol. 11, pp. 928-934.*

(Continued)

*Primary Examiner* — Anastasia Midkiff
(74) *Attorney, Agent, or Firm* — Oliff & Berridge, PLC (57) ABSTRACT

Since measurement of magnetostriction is accompanied by measurement of magnetization, magnetostriction and magnetization are measured conventionally by separately prepared devices, with efforts for observing the same region of the sample. Measurement of the magnetostriction is difficult due to the difficulty of compensation and calibration. The value of magnetostriction coefficient in low temperature region cannot be correctly determined. A convenient method which can measure magnetostriction and magnetization simultaneously at the same region of the sample and at the same time is developed by combining the method of measurement of magnetostriction by X-ray diffraction and the method of measurement of magnetic X-ray diffraction. The observed X-ray diffraction intensity as a function of the magnetic field from the sample can be separated to symmetric component and asymmetric component, which contain signals proportional to the magnetostriction and magnetization, respectively.

9 Claims, 7 Drawing Sheets

FOREIGN PATENT DOCUMENTS

| | | |
|---|---|---|
| JP | B2-3521010 | 2/2004 |
| JP | B2-3526750 | 2/2004 |

OTHER PUBLICATIONS

Bormio-Nunes et al., "Volume Magnetostriction and Structure of Copper Mold-cast Polycry Alloys", Dec. 30, 2004, Journal of Applied Physics (print 2005) vol. 97, 033901 pp. 1-6.*

Yang, Ning, Thesis, "Synchotron Diffraction Studies of Spontaneous Magnetostriction in Rare Earth Transition Metal Compounds", 2004, Iowa State University.*

Etienne Du Trémolet De Lacheisserie. "Magnetostriction: Theory and Applications of Magnetoelasticity," CRC Press, Boca Raton, 1993.

Arakawa et al., "Observation on Magnetostriction by X-rays in Iron," presented at the Joint Symposium on Magneto-Science 2004, held from Dec. 1-3, 2004 at Yokohama National University in Yokohama, Japan.

Al-Jiboory et al., "Study of the Magnetostrictive Distortion in Single Crystal Terfenol-D by X-Ray Diffraction," *IEEE Transactions on Magnetics*, vol. 26, No. 5, Sep. 1990, p. 2583-2585.

* cited by examiner

Temperature, $T = t_i$

FIG. 7

FIG. 8

METHOD AND DEVICE FOR SIMULTANEOUS MEASUREMENT OF MAGNETOSTRICTION AND MAGNETIZATION

TECHNICAL FIELD

The present invention relates to a method enabling the measurement of magnetostriction and magnetization by diffraction method at the exact coextensive volumes of the sample, and the method for the creation of a magnetic substance comprising a standard sample for calibration according to said measurement method, a magnetic substance comprising a standard sample for calibration according to said measurement method, and a device such as sensors to measure magnetostriction which are calibrated using said standard calibration sample, and also a device for simultaneous measurement of magnetostriction and magnetization.

BACKGROUND ART

Magnetostriction is a small deformation caused by the magnetization of magnetic substances. The deformation between dimensions at the demagnetized state of a magnetic substance and at saturation magnetization state is conversed into an amount per unit length, which is called "saturation magnetostrictive coefficient", or simply "magnetostrictive coefficient". The magnetostrictive coefficient shows different values for the easy axis magnetization and the hard axis magnetization, and also shows elongation and contraction in accordance to the magnetization. Magnetostrictive coefficient also changes its value as a function of temperature. In the fields of physics and engineering, the magnetostrictive coefficient having these characteristics is one of the basic properties unique to the substance.

Recently, magnetostriction in the field of industry, is utilized as a magnetostrictive actuator (see Japanese Patent No. 3332125 Magnetostrictive actuator for reference) or a magnetostrictive sensor utilizing the reverse effect of magnetostriction (see Japanese Patent No. 3521010 "Magnetostrictive sensor" for reference), or a magnetostrictive torque sensor (see Japanese Patent No. 3526750 "Magnetostrictive torque sensor" for reference), or a magnetostrictive stress measurement (see Japanese Patent No. 2771433 "A measurement method of magnetostrictive stress of tubes" for reference).

The magnetostrictive coefficient as a basic property unique to the substance, is generally measured by strain gauge method or capacitance method (for example, see Etienne du Trémolet de Lacheisserie Magnetostriction: theory and applications of magnetoelasticity, CRC Press, Boca Raton, 1993 for reference). This is classified as an external magnetostriction, which is an amount obtained by macroscopic observation of the deformation of a magnetic substance between dimensions at demagnetized state and at saturation magnetization state. For the measurement of the magnetostrictive coefficient in the external mode with this method, it must be noted that the confirmation that the magnetization is sufficiently approaching to the saturation is necessary.

As opposed to this, the crystallographical magnetostrictive coefficient is known. This value is not detected except by using an X-ray diffraction method or a neutron diffraction method by measuring a change in the lattice spacing. Especially, in a magnetic substance consisting of two or more kinds of elements, the magnetostriction defined as the relative change in the location of the atoms in a unit cell is called an internal magnetostriction (see above mentioned Magnetostriction: theory and applications of magnetoelasticity for reference).

Now, the macroscopic external magnetostrictive coefficient and crystallographical magnetostrictive coefficient may be different values, according to the definition. However, if the sample is a single crystal consisting of one kind of element, our interest is their values at saturation magnetization the values would show the same.

As for the method of measurement of this crystallographical magnetostrictive coefficient, the above mentioned X-ray diffraction method and neutron diffraction method are useful, but conventionally, both were poor in resolution, and could only be applied to substances that showed large magnetostrictive coefficients. Therefore, X-ray diffraction method was not applied as a practical method (see above mentioned Magnetostriction: theory and applications of magnetoelasticity for reference), and was seldom used.

Figure 1:
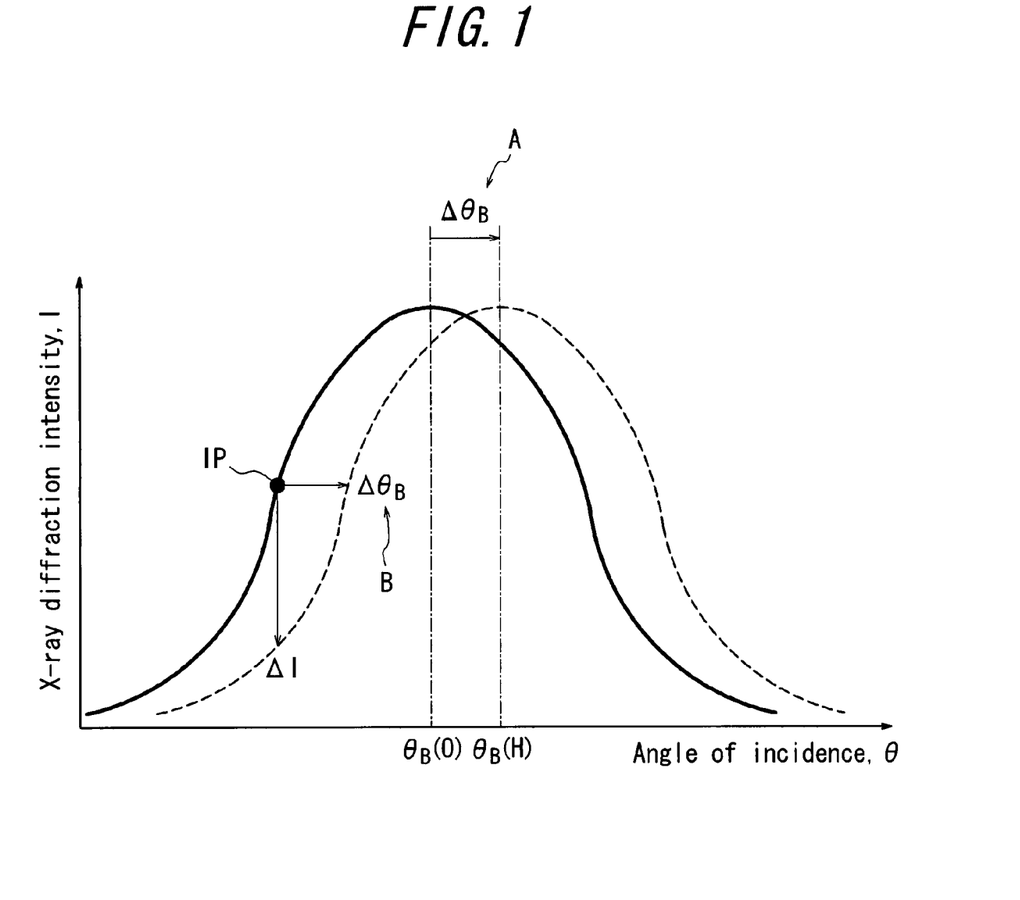
FIG. 1 is a schematic diagram explaining a rocking curve which shows the relation between the angle θ of incident X-rays to the sample, and the X-ray diffraction intensity I, which is obtained using X-rays diffraction method in order to exhibit the measurement principle of the Bragg angle shift.

FIG. 1 is a schematic diagram to explain exemplifies the relation between the angle of incidence $\theta$ and the intensity of X-ray diffraction I of a rocking curve, in which the vertical axis refers to the intensity of X-ray diffraction I and the horizontal axis refers to the angle of incidence $\theta$. In FIG. 1, the rocking curve profile $I(0, \theta)$ at the demagnetized state is shown in a solid line, and the rocking curve profile $I(H, \theta)$ at the saturation magnetization state at magnetic field H is shown in a broken line, for a sample. In the conventional crystallographic method for measuring magnetostriction using X-ray diffraction, scanning the incident angle by a high resolution goniometer, and the Bragg angle (the angle that gives the peak point for the rocking curve profile in FIG. 1) at the demagnetized state $\theta_B(0)$ and the Bragg angle at the saturation magnetization state $\theta_B(H)$ were measured, and as shown in FIG. 1 as A, a Bragg angle shift $\Delta\theta_B$ was calculated from the difference between the $\theta_B(0)$ and $\theta_B(H)$, which was converted into the change of the lattice spacing in order to calculate the magnetostrictive coefficient. However, the rocking curve being flat near the peak point, determining the angle of the peak point often gave uncertainty, and thus the direct measurement of the difference between these angles was not useful.

As opposed to this, in recent years, the present inventor et al. have improved the sensitivity with the X-ray diffraction method by two orders, as compared to the conventional method, and have provided a practical accuracy for the measurement on one of the typical magnetic materials. (See Arakawa, Etsuo; Nishigaitsu, Hidetaka; Mori, Koichi; Maruyama, Koh-ichi, Magnetic Science Joint Symposium 2004, 2004, 3AP22 for reference)

Specifically, the present inventor et al. have presented a method for determining the magnetostrictive coefficient with high sensitivity (Non-patent literature 3), in which the diffractometer was fixed near the intensity inflexion point (IP) of the rocking curve (see FIG. 1 for reference), while the diffraction intensity change $\Delta I$ caused by the existence or non-existence of magnetization was measured with sufficient photon statistics, which was compared to the amount calculated by differentiation of the rocking curve, and as indicated in FIG. 1 as B, the Bragg angle shift $\Delta\theta_B$ was calculated by the division of $\Delta I$ and $I(0,\theta)$ as will hereinafter be described, which was converted into the change of lattice spacing. The outlines of this method will be described below.

Figure 2:
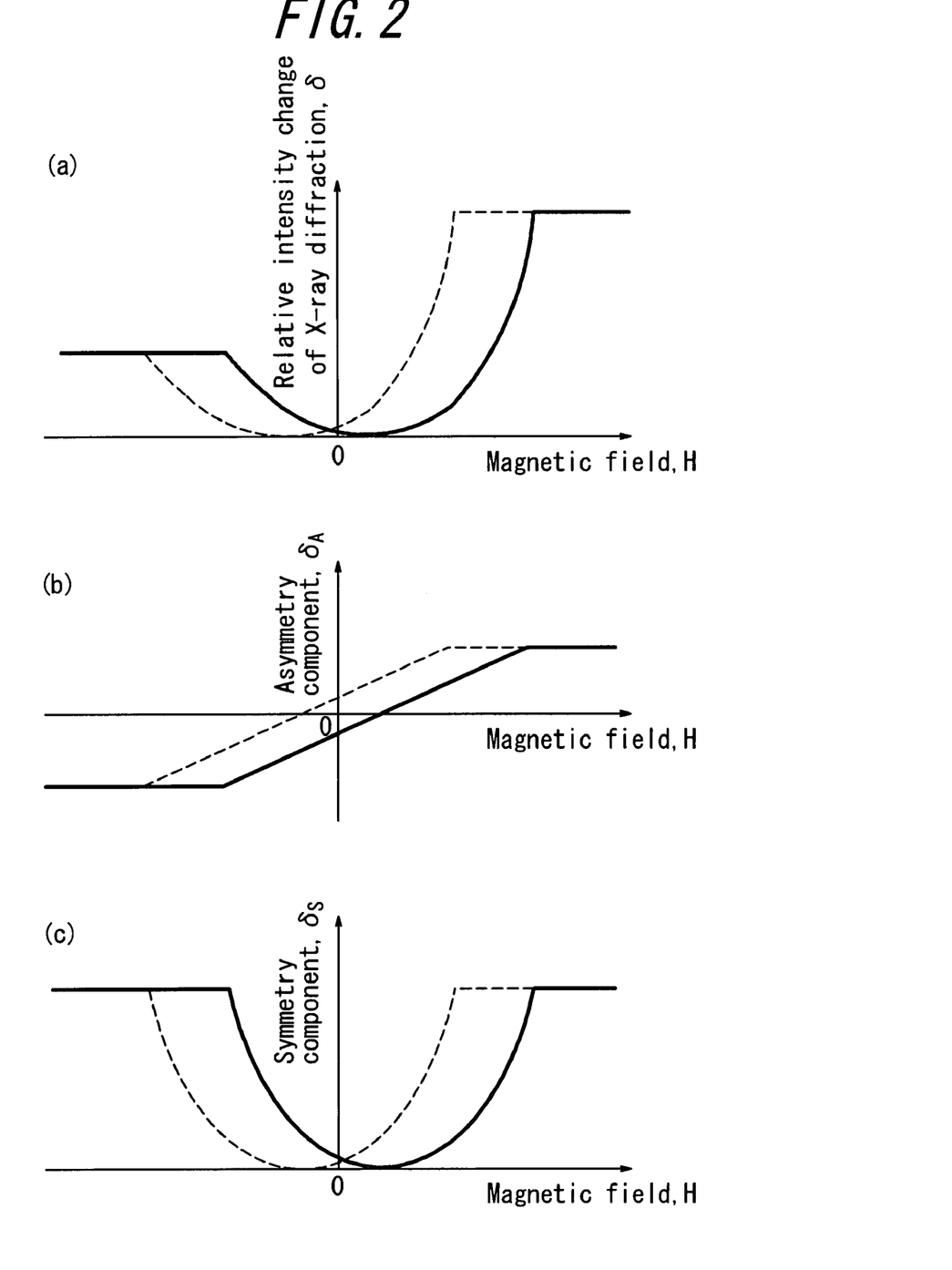
FIG. 2(a) is a schematic diagram showing the relation between the relative intensity change $\delta$ of X-ray diffraction as a function of magnetic field H.
FIG. 2(b) is a schematic diagram showing the relation between the asymmetry component $\delta_A$ to the magnetic field of the relative intensity change $\delta$ of X-ray as a function of magnetic field H.
FIG. 2(c) is a schematic diagram showing the relation between the symmetry component $\delta_S$ to the magnetic field of the relative intensity change $\delta$ of X-ray diffraction as a function of magnetic field H.

FIG. 2(a) shows a schematic diagram to explain the relative intensity change of X-ray diffraction in accordance to the strength of magnetic field H, in which the vertical axis refers to the relative intensity change $\delta$ axis, and the horizontal axis refers to the magnetic field H axis. FIG. 2(b) shows a schematic diagram to explain the relation between the strength of magnetic field H and the asymmetry component $\delta_A$ to the magnetic field of the above mentioned relative intensity change $\delta$, in which the vertical axis refers to the asymmetry component $\delta_A$, and the horizontal axis refers to the magnetic field H axis. FIG. 2(c) shows a schematic diagram to explain the relation between the strength of magnetic field H and the symmetry component $\delta_S$ to the magnetic field of the above-mentioned relative intensity change $\delta$, in which the vertical axis refers to the symmetry component $\delta_S$, and the horizontal axis refers to the magnetic field H axis. In FIG. 2(a), the solid line represents the property measured during ascending magnetic field, and the broken line represents the property measured during the descending magnetic field, and in FIGS. 2(b), 2(c), the solid line represents the property during ascending magnetic field (equivalent to the hereinafter described equation [No. 3] and equation [No. 4] respectively), and the broken line represents the corresponding property calculated during descending magnetic field (equivalent to the opposite signs of $\delta_A$ and H in hereinafter described equation [No. 3] and H in hereinafter described equation [No. 4], respectively). The relative intensity change $\delta$ of X-ray diffraction shown in FIG. 2(a) is expressed as follows

[No. 1]
$$\delta(H, \theta) = \frac{\Delta I(H, \theta)}{\bar{I}(0, \theta)} = \frac{I(H, \theta) - \bar{I}(0, \theta)}{\bar{I}(0, \theta)} \quad (1)$$

where

[No. 2]
$$\bar{I}(H, \theta) = \frac{I(H, \theta)|_{0<dH/dt} + I(-H, \theta)|_{dH/dt<0}}{2} \quad (2)$$

$I(H, \theta)$ is the diffraction intensity at magnetic field strength H, observed at an angle of incidence $\theta$ close to the Bragg angle. If the relative intensity change of the X-ray diffractions was measured at ascending magnetic field $0<dH/dt$ and at descending magnetic field $dH/dt<0$, the component $\delta_A$ asymmetry to the magnetic field shown in FIG. 2(b), and the component $\delta_S$ symmetry to the magnetic field shown in FIG. 2(c) are given,

[No. 3]
$$\delta_A(H, \theta) = \frac{\delta(H, \theta)|_{0<dH/dt} - \delta(-H, \theta)|_{dH/dt<0}}{2} \quad (3)$$

[No. 4]
$$\delta_S(H, \theta) = \frac{\delta(H, \theta)|_{0<dH/dt} + \delta(-H, \theta)|_{dH/dt<0}}{2} \quad (4)$$

respectively. The symmetry component $\delta_S$ to the magnetic field is the subtraction ($\delta_S = \delta - \delta_A$) when $\delta_A$ is subtracted from $\delta$. For evaluating the magnetostrictive coefficient, in the relative diffraction intensity change $\delta$, only the symmetry component $\delta_s$ to the magnetic field, was used, and the asymmetry component $\delta_A$ to the magnetic field, was not used.

By combining the rocking curve profile at the demagnetized state $I(0, \theta)$ shown in a solid line in FIG. 1 with its differential coefficient $dI(0, \theta)/d\theta$, another relative diffraction intensity change $D(\theta)$ is defined.

[No. 5]
$$D(\theta) = -\frac{dI(0, \theta)}{d\theta} \cdot \frac{\Delta \theta_B}{I(0, \theta)} \quad (5)$$

By comparing this relative intensity change $D(\theta)$ to the symmetry component $\delta_S$ obtained in equation [No. 4], the difference from the Bragg angle $\theta_B$ at the demagnetized state, in other words, the shift $\Delta \theta_B$ of the rocking curve (indicated in FIG. 1 as B) can be determined.

The fact that the magnetostrictive coefficient $\lambda_{100}$, when the magnetization is oriented along one of the magnetization easy axis, neglecting the volume change, can be obtained using the shift $\Delta \theta_B$ of the rocking curve by the following equation

[No. 6]
$$\lambda_{100}(H) = 2(\cot\theta_B)\Delta\theta_B = \frac{\delta_S(H, \theta)}{-\frac{1}{2} \cdot \frac{dI(0, \theta)}{d\theta} \cdot \frac{\tan\theta_B}{I(0, \theta)}} \quad (6)$$

as a value with a practical accuracy at the saturation magnetization state, is a method which the present inventor et al. have made publicly known (See Arakawa, Etsuo; Nishigaitsu, Hidetaka; Mori, Koichi; Maruyama, Koh-ichi, Magnetic Science Joint Symposium 2004, 2004, 3AP22 for reference.).

This magnetostriction measured by the publicly known method, is not the average value on the whole volumes of the bulk in the sample, but a local value of the volumes near the surface where the X-ray beam irradiates and interacts while diffraction. By using this publicly known method, magnetostriction can be measured nonelectrically, noncorrecting, and noncontactually by X-rays. In the experiments, for the shift $\Delta \theta_B$ and the magnetostriction $\lambda_{100}$, the dependency on $\theta$ could not be detected. Thus, in the left hand side of equation [No. 6], it could simply be noted $\lambda_{100}(H)$.

Under extreme conditions such as low temperature, or high magnetic field, being under the effect of thermal contraction or thermal conduction and magnetoresistance effect peculiar to electric devices, the calibration of the devices to measure the magnetostriction may sometimes be difficult. Under such extreme condition, property measurement devices may not be able to work with its own sensitivity as it worked at room temperature (See above mentioned "Theory of High-Temperature Magnetostriction" for reference.).

Figure 3:
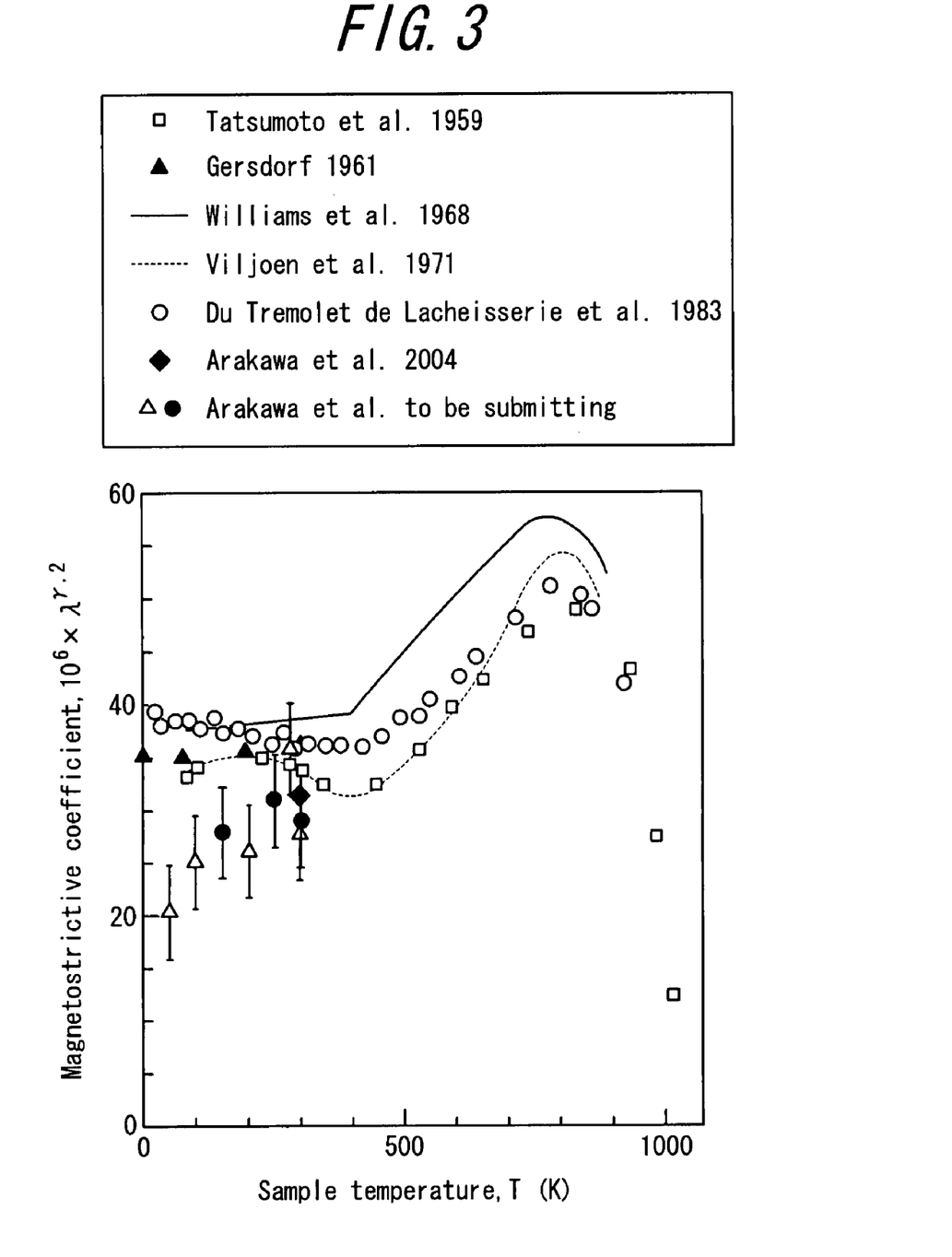
FIG. 3 is an explanatory diagram exemplifying the result of a temperature dependent measurement of magnetostrictive coefficient of iron $\lambda^{\gamma,2}$.

For example, concerning the magnetostrictive coefficient of iron at low temperature close to 200K, there are various opinions as shown in FIG. 3 (See above mentioned Magnetostriction: theory and applications of magnetoelasticity and Magnetic Science Joint Symposium 2004, 2004, 3AP22 for reference.). Here, the vertical axis in FIG. 3 is $10^6 \times \lambda^{\gamma,2}$ axis and the horizontal axis represents the sample temperature T (K). The reason for various reports to arise in the magnetostrictive coefficient of iron is the difficulty of its calibration and correction at low temperature and high magnetic field. More specifically, at the present state, even for industrially important materials such as iron, the scientific basic property which ought to be a universal value unique to a substance, is not determined precisely whether they are correctly measured or not.

For measuring the magnetostrictive coefficient, owing to definition, it is necessary to confirm these magnetization states of the sample material to be measured, that they are in the demagnetized state and saturation magnetization state. In other words, for the measurement of magnetostriction, the measurement of magnetization on the sample material is necessary.

Conventionally, it is commonly known to provide two devices for measuring magnetostriction and magnetization respectively. Therefore, one must use a device based on the principle of magnetostriction measurement, having a sensitive probe at the region of interest volume of the sample, together with a device based on the principle of magnetization measurement, having a sensitive probe at the region of interest volume of the sample and efforts were made to measure them at the same volumes of the sample. As long as two devices are used for the observation of magnetostriction and magnetization at the same volume, ultimately, there are cases in which it has to be assumed that the observations are performed at the coextensive volumes.

In many cases, this assumption that the magnetostriction and the magnetization are observed at the coextensive volumes is accepted. But the fact that the devices are different for the measurements of the magnetostriction and the magnetization, means that both devices must be prepared respectively. In addition, in cases where the principles or the sensitive volumes of the probes are different, or, where either of the measurements cannot be preferably done under a certain condition, the assumption that the observations are performed at the coextensive volumes cannot always be accepted. The conventional method is insufficient in this point.

Under extreme conditions such as low temperature, whereas such a property as the magnetostriction of iron, one of the typical magnetic substances, has not been well determined, a standard sample for calibration of devices with known features, cannot be found at the moment.

For the measurements of the magnetostriction and the magnetization, if the observations at the coextensive volumes are not accepted, since too much magnetic field strength must be applied in order to saturate the magnetization, it may be harmful on its correction.

Thus, it is clear that the development of a method which enables the measurement of the magnetostriction and the magnetization at the exact coextensive volumes, without assumption, and under any measurement conditions, is useful.

DISCLOSURE OF THE INVENTION

Problems to be Solved by the Invention

The objective of the present invention is to provide a method which enables the measurements of magnetostriction and magnetization at the exact coextensive volumes, a method for adapting a data set of the crystallographic magnetostrictive coefficient to the devices to measure the macroscopic external magnetostrictive coefficient and a magnetic substance such as a standard sample for calibration evaluated using said methods, devises such as sensors calibrated using these standard samples for calibration evaluated using said methods, and to provide a device for simultaneous measurements of the magnetostriction and the magnetization using the above methods.

Methods to Solve the Problem

The present inventors have, surprisingly, realized that the value obtained by combining asymmetry component $\delta_A$ and symmetry component $\delta_S$ to the magnetic field separated from the relative intensity change $\delta$ of X-ray diffraction

[NO. 7]

$$R'_a(H, \theta) = \frac{\delta_A(H, \theta)}{1 + \delta_S(H, \theta)} \qquad (7)$$

$$= \frac{I(H, \theta)|_{0<dH/dt} - I(-H, \theta)|_{dH/dt<0}}{I(H, \theta)|_{0<dH/dt} + I(-H, \theta)|_{dH/dt<0}}$$

can be used to obtain the relative magnetization of the sample. $R'_a(H, \theta)$ can also be determined from diffraction intensity $I(H, \theta)$ which constitutes the relative intensity change $\delta$. $R'_a(H, \theta)$ is a function of H, and the value at the saturation magnetization is equal to the asymmetry ratio $R_a$ of X-ray magnetic diffraction. According to the experiment, $R'_a(H, \theta)$ did not depend on the angle of incidence $\theta$, thus it will hereafter be described simply as $R'_a(H)$.

The ratio of $R'_a(H)$ to its saturation value $R_a$

[No. 8]

$$\frac{M(H)}{M_S} = \frac{R'_a(H)}{R_a} \qquad (8)$$

is equal to the relative magnetization $M(H)/M_s$. Here, M(H) is the value of the saturation magnetization of the sample, and $M_s$ is the value of the saturation magnetization of the sample.

Usually, for the asymmetry ratio $R_a$ of X-ray magnetic diffraction, integrated intensity integrated over the angle of incidence θ or the peak intensity of the rocking curve is used. Equation [No. 7] is different in that it uses the partial intensity at the angle of incidence θ.

In the measurement of the magnetization which is necessary to measure the magnetostrictive coefficient, it is enough to measure the relative value of the magnetization to the saturation value, because we would confirm the saturation magnetization as a function of the magnetic field.

On the other hand, the magnetostrictive coefficient is the saturation value of $\lambda_{100}(H)$ obtained from equation [No. 6], and the $\lambda_{100}(H)$ which is at the magnetization process at magnetic field H, is related to the value of relative magnetization at equation [No. 8]. Meanwhile, the asymmetry component $\delta_A$ to the magnetic field in equation [No. 3] has had an important role in the present invention, but it must be formulated that it was not necessary for the publicly known method of magnetostriction measurement.

The present inventors have discovered that, by using these values, the symmetry and asymmetry components to the magnetization field, which are obtained by observing the relative diffraction intensity change by developing the conventionally known method it is possible to provide a convenient method by which the absolute value of magnetostrictive coefficient and the relative value of the magnetization can be determined simultaneously. The present invention is based on such knowledge and the method for the simultaneous measurements of the magnetostriction and the magnetization according to the present invention is characterized in that it measures the relative diffraction intensity change $\delta$ which is measured at ascending magnetic field and measured at descending magnetic field each at the said coextensive volumes of said sample, from which it obtains the asymmetry component $\delta_A$ and the symmetry component $\delta_S$ to the magnetic field H from the relative diffraction intensity change $\delta$ at said volumes of said sample, and obtains magnetostrictive coefficient of said volumes of said sample based on said symmetry component $\delta_S$, and obtains relative magnetization of said volumes of said sample based on the value obtained by recomposing said asymmetry component $\delta_A$ and symmetry component $\delta_S$, on measuring the magnetostriction and the magnetization at the coextensive volumes of the sample simultaneously.

Figure 4:
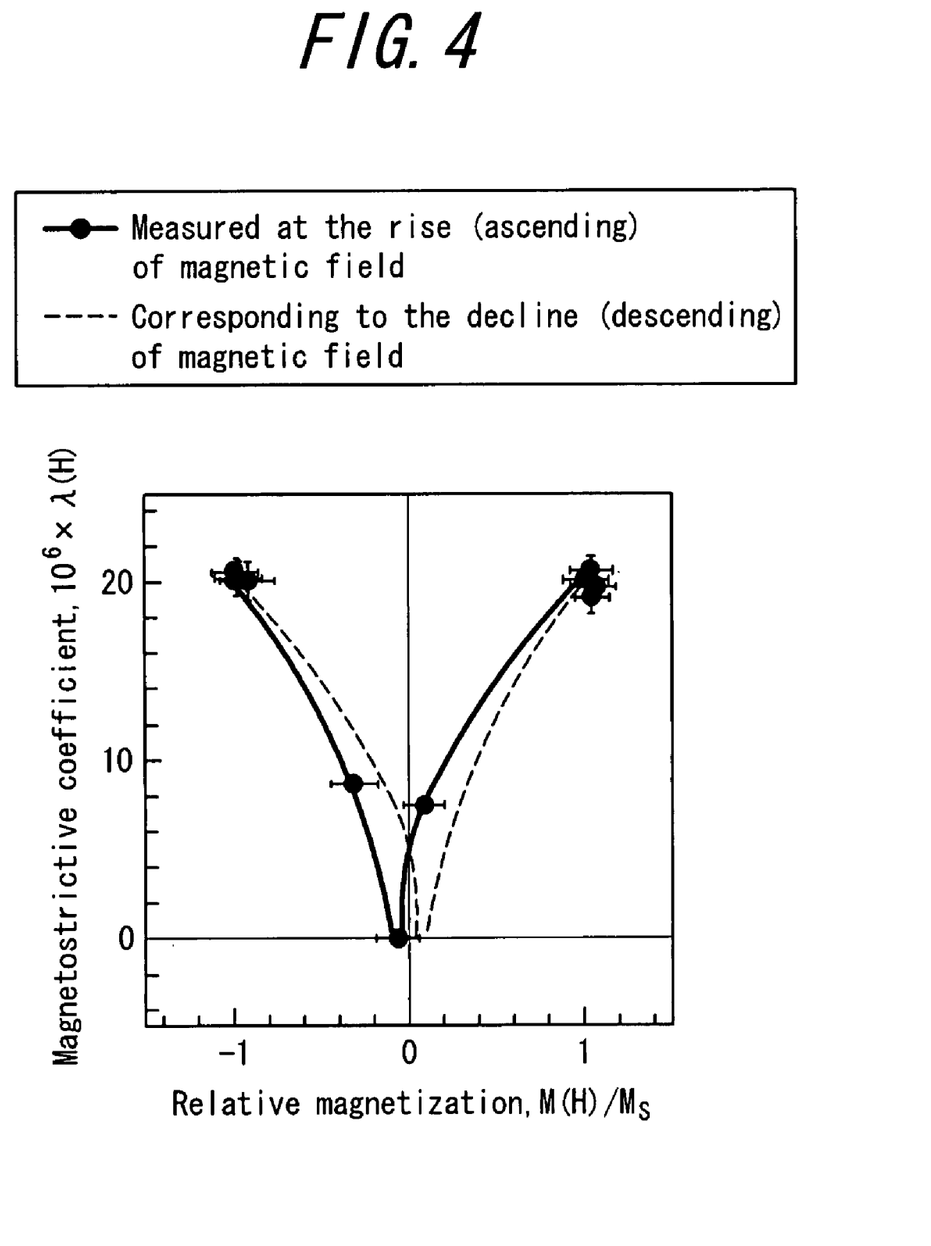
FIG. 4 is an explanatory diagram explaining the result of a magnetization dependent measurement of magnetostriction of iron.

The symmetry and asymmetry components $\delta_S$ and $\delta_A$ are values obtained by the measurement of the originally common relative intensity change $\delta$, which is once separated based on its symmetry to the magnetic field, then subsequently combined. In other words, the present invention relates to a method in which the two kinds of values, absolute value of the magnetostriction and the relative value of the magnetization can be measured simultaneously at the coextensive volumes by the same device, by the same X-ray probe, and by the same device as shown in FIG. 4. Here, in FIG. 4, the vertical axis is the axis of magnetostrictive coefficient $10^6 \times \lambda(H)$, and the horizontal axis is the relative magnetization $M(H)/M_s$.

In addition, by the present invention, it has been made clear that it is possible to provide a method enabling the correct calibration of conventionally known devices for measuring magnetostriction under extreme conditions such as low temperature and high magnetic field, having corrections for quantitative measurement. More specifically, from the results of the observation of crystallographical magnetostrictive coefficient obtained by measuring the change of the lattice spacing of a single crystal, it has been discovered that it is efficient to list the calibration table that is appropriate for the calibration of devices for measuring macroscopic external magnetostriction using a plurality of standard samples. This method for calibration is characterized in that it is not affected by the magnetic resistance effect or the thermal expansion coefficient.

Here, the magnetostriction property refers to characteristics of properties such as magnetic field dependence, or magnetization dependence or temperature dependence, or magnetization orientation dependence.

The measurement of diffraction intensity under the magnetic field in the present invention by X-ray diffraction under the magnetic field, can be replaced by diffraction of neutron diffraction under the magnetic field. Here, the X-ray diffraction under the magnetic field refers to resonant magnetic diffraction or non-resonant magnetic diffraction.

EFFECTS OF THE INVENTION

The present invention is a method for measuring a property called magnetostriction, and is able to provide a new magnetostrictive coefficient measuring method characterized in that the observation is performed with the measurement of the magnetization of the sample by diffraction method.

Moreover, the present invention is a device for evaluating the characteristics of a property called magnetostriction and is able to provide a standard calibration sample produced, including the magnetostrictive coefficient evaluated by the method of measuring the magnetostrictive coefficient by the diffraction method in the specification of the performance table.

Further, the present invention is able to provide a new method for the calibration of devices for measuring macroscopic external magnetostriction characterized in that crystallographic magnetostrictive coefficient measured by observing the change of the lattice spacing is utilized.

Furthermore, the present invention is able to provide devices for measuring magnetostriction such as sensors, calibrated using the new method for the calibration of devices for measuring macroscopic external magnetostriction characterized in that crystallographic magnetostrictive coefficient, measured by observing the change of the lattice spacing, is utilized.

Moreover, the present invention is able to provide products which have been evaluated with the properties of devices for measuring magnetostriction such as sensors, calibrated using the new method for the calibration of devices for measuring macroscopic external magnetostriction characterized in that crystallographic magnetostrictive coefficient, measured by observing the change of the lattice spacing, is utilized.

According to the present invention, in order to execute the method in which the values of the magnetostriction and the magnetization are measured using X-rays, with the same X-ray probe and the same device, it is preferable to use the synchrotron X-radiation. The synchrotron X-radiation being of high intensity, realizes a practical measurement time and can be used for the measurement of relative magnetization which utilizes magnetic diffraction.

Thus, the embodiment of the present invention, for example, may be the resonant magnetic diffraction with the π polarized incidence which is tuned to X-ray absorption edge energy, or, the non-resonant magnetic diffraction. By using the synchrotron X-radiation as the X-ray source, both measurements in both of the magnetic diffraction become possible.

There are intensity changes to the configuration of magnetic diffraction. Thus, it is possible to measure the parallel and perpendicular components of the magnetostrictive coefficient to the magnetization and to focus on various coefficients of magnetostriction such as volume magnetostriction, by selecting of the orientation of magnetization and the configuration of the magnetic diffraction.

Moreover, a magnetic substance evaluated on the magnetization and the magnetostriction at synchrotron radiation facilities according to the present invention, can be used as a converter of supersonic waves in the case of its usage as a magnetostriction material. For the application of supersonic waves, there is its use in measurement and communications as a transmission signal, and there is also a use in power machines for use of its energy.

An example of a use in machines is to apply an appropriate direct current biased magnetic field $H_{DC}$ to a ferromagnetic substance, thereby making it in a certain magnetization $M(H_{DC})$ state, and if a small alternating magnetic field $\Delta H$ is applied, a change in size $\Delta\lambda$ results along with the change in magnetization $\Delta M$. This can be used as a magnetostrictive vibrator.

Here, the relation between the magnetic field and the magnetization and the relation between the magnetic field and magnetostriction are generally different depending on the shape of the sample, hence the relations are not universal. The relation between the magnetization and the magnetostriction does not depend on the shape of the sample, and therefore the relations are suitable for characterizing the magnetostrictive materials. The magnetostriction and the magnetization are affected by the stress and temperature of the magnetostrictive material, and thus the characterizations by the measurements at the coextensive volumes has a special advantage. In addition, the magnetization may be enough to evaluate the relative value to the saturation magnetization.

For the above said usage of supersonic waves as power, it is utilized for washing, processing, welding, dispersing, mixing, aggregating, and other uses such as diagnosing and therapy for medical purposes [For example, see "Shinjidai no jiseizairyou" chap. 14, Magnetic materials (Toshio Wakao), Industrial Research Association, pages 207-214, 1981, edited by Mitoukakougijyutsu Association for reference.].

Moreover, a magnetic substance characterized by the present invention on the magnetostriction and the magnetization can be used as a standard sample to calibrate characterized devices which measure a property of magnetostriction. Samples characterized on the magnetostriction and the magnetization by the present invention are applicable as a standard sample for device calibration under extreme conditions such as low temperature and high magnetic field, where the calibration of conventional electrical devices to measure the magnetostriction, for example, strain gauge or capacitance bridge, has been especially difficult.

Suitable standard sample for calibration is a single crystal. For a single crystal sample, it is convenient that the macroscopic value of external magnetostriction and the crystallographical value of magnetostriction obtained by observing the change of the lattice spacing would show the same value when they are saturated value.

Further, the present invention is able to provide electrical devices for measuring macroscopic external magnetostriction, calibrated using standard samples for calibration characterized by measuring the magnetostrictive coefficient according to the present invention obtained by observing the change of the lattice spacing. By using the conventionally known electrical devices for measuring magnetostriction, calibrated with the standard sample for calibration characterized according to the present invention without bringing the sample for the measurement into the synchrotron radiation facility, the present invention is practicable at any conventional place without restriction.

Furthermore, the present invention is a device which measures the magnetostriction and magnetization at the coextensive volumes of the sample simultaneously and is able to provide a device for the simultaneous measurement of magnetostriction and the magnetization, characterized by a diffractometer which measures the relative diffraction intensity change of $\delta$ at ascending magnetic field and the descending magnetic field respectively at said coextensive volumes of said sample, a calculation means which obtains the asymmetry component $\delta_A$ and symmetry component $\delta_S$ to the magnetic field H from the relative diffraction intensity change $\delta$ at the above mentioned ascending magnetic field and the descending magnetic field, a magnetostrictive coefficient calculation means which obtains magnetostrictive coefficient $\lambda_{100}$ of said volumes of said sample based on said symmetry component $\delta_S$, and a relative magnetization calculation means which obtains the relative magnetization $M/M_s$ of said volumes of said sample based on the value $R'_a$ obtained by recomposing said asymmetry component $\delta_A$ and symmetry component $\delta_S$, and a magnetostriction and magnetization display means which displays the said obtained magnetostrictive coefficient and the relative magnetization on the screen simultaneously.

A BRIEF DESCRIPTION OF THE DRAWINGS

FIGS. 7(a) to 7(c) shows the principal of strain gauge calibration method and its usage with a number line, where FIG. 7(a) is an explanatory diagram which shows all the output resistance values of the strain gauge on the calibration table, the known value of magnetostrictive coefficient, and all the values relating to object X to be measured at temperature $t_i$, and FIG. 7(b) is an explanatory diagram showing the part on iron of the calibration table mentioned in FIG. 7(a), and the part related to the idea for obtaining the magnetostrictive coefficient of the object X to be measured, and the part on nickel of the calibration table mentioned in FIG. 7(a).

BEST MODE FOR CARRYING OUT THE INVENTION

The First Embodiment

The case in which the present invention is utilized for the preparation of the standard sample for the first calibration of a device for measuring the magnetostrictive coefficient will be explained below with reference to the embodiments.

In the first embodiment, a single crystal sample of ferromagnetic substance, for example iron is prepared, and at a synchrotron radiation facility, by X-ray diffraction method according to the present invention, the measurement of magnetostriction property together with the measurement of the magnetization of said sample is performed. More specifically, the magnetostriction property of said sample is obtained from the shift amount of the Bragg angle, and the magnetization property is obtained as relative magnetization from the normalized asymmetry ratio of resonant magnetic scattering together with the magnetostriction.

Figure 5:
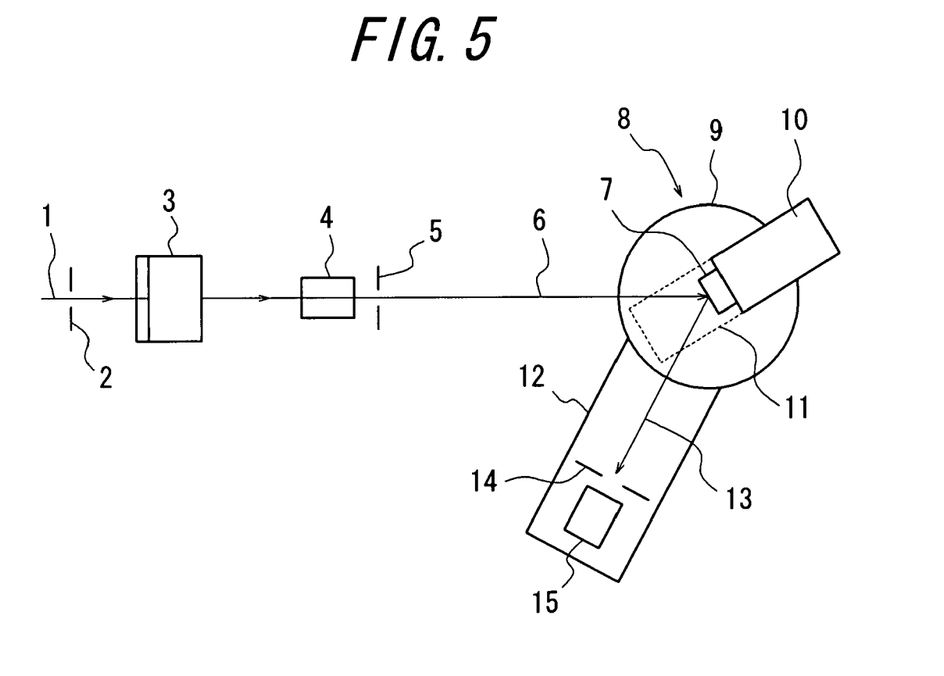
FIG. 5 is a schematic diagram showing an example of the constitution of a device in a top view, which measures the magnetostriction and the magnetization simultaneously according to the present invention.

The device for measurement is a goniometer arranged for resonant magnetic diffraction as shown in FIG. 5. Here, sign 1 is the bending magnet, 2 is the beam line slit, 3 is the silicon double-crystal monochromator, 4 is the incident X-ray monitoring in chamber, 5 is the sample slit, 6 is the incident monochromatized X-rays, 7 is the sample, 8 is the goniometer, 9 is the electromagnet on the goniometer, 10 is the refrigerator for sample temperature control, 11 is the shroud, 12 is the 2θ arm of the diffractometer, 13 is the diffraction X-rays, 14 is the receiving slit, and 15 is the X-ray detector. Compared to the single crystal sample of iron 7, the incident X-ray 6 is a π polarized, K absorption edge energy of iron. Sample 7 is set to temperature T by refrigerator 10. The diffraction intensity is measured applying the magnetic field by electromagnet 9 in the orientation of easy magnetization [001] of sample 7.

The angle of incident θ of sample 7, is desired to be fixed near the inflection point of the low angle and the high angle side of the rocking curve (point IP in FIG. 1 is near the inflection point of the low angle side). The measurements near both inflection points fulfill the best conditions for the measurement of the magnetostrictive coefficient and the measurement of magnetization, and are able to determine the magnetostrictive coefficient at the highest accuracy.

The measurement of the relative diffraction intensity change of diffraction intensity δ(H,θ) is performed at a sufficient accuracy of photon statistics, for every set of ascending magnetic field H and descending magnetic field –H, specifically $\delta(H, \theta)|_{0<dH/dt}$ and $\delta(-H,\theta)|_{dH/dt<0}$. Other than this, for the measurement of the absolute value of the magnetostrictive coefficient, the intensity profile I(θ) of the rocking curve at the demagnetized state is measured. Especially, around the angle of incident θ used for the measurement of δ(θ), should be measured with sufficient accuracy of photon counting for differentiation coefficient dI(θ)/dθ obtained by calculating the finite differences. The derivation method is as equation [No. 6]. The magnetostrictive coefficient is not restricted to $\lambda_{100}$ but may be replaced with $\lambda_{111}$, $\lambda^{\gamma,2}$, $\lambda^{\epsilon,2}$.

The magnetization is obtained from the normalized asymmetry ration of resonant magnetic scattering. The method of derivation is as equation [No. 8].

The magnetization dependent result of magnetostrictive coefficient approaching to the saturation magnetization, can be showed as a graph as shown in aforementioned FIG. 4. From the measurement result obtained by the present embodiment as shown in FIG. 4, it can be ascertained that, even if the magnetic field is changed, the magnetization does not change. The maximum value of the relative magnetization axis (the horizontal axis) is normalized, and represents the saturation magnetization. The value of the magnetostriction axis (the vertical axis) for this value is the magnetostrictive coefficient.

The Second Embodiment

The present invention for use in the evaluation of standard sample for calibration of the macroscopic magnetostriction measurement device at low temperature will be explained below with other embodiments.

In this second embodiment, a ferromagnetic substance, for example iron, is prepared. The crystallographic magnetostrictive coefficient observed microscopically by X-rays, and the external magnetostrictive coefficient observed macroscopically may not be the same value, but in the case of iron, a single crystal sample, by observing the change of the lattice spacing by X-rays, presents the same value, and this property is utilized.

At a synchrotron radiation facility, by the X-ray diffraction method, by the same method as the former embodiment, the magnetostriction property of the sample are measured together with the magnetization. More specifically, the magnetostriction property of said sample is obtained from the Bragg angle shift, and the magnetization property is obtained as relative magnetization from the normalized asymmetry ratio of the resonant magnetic scattering together with the magnetostriction.

The magnetization dependent result of magnetostrictive coefficient obtained by observing the change of the lattice spacing by X-rays, for which the sample temperature T was varied from 50 K to room temperature, can be marshaled as a graph as shown in aforementioned FIG. 3.

Two kinds of physical quantities necessary for the calibration are (t, λ(t$_i$)) for each standard sample. Here, T=t$_i$ (i=1,2, 3. . . ) is the set temperature, λ(t$_i$) is a crystallographical magnetostrictive coefficient measured by observing the change of the lattice spacing by X-rays at temperature t$_i$ according to the present invention. It is preferable that the set temperature is appropriately subdivided. This magnetostrictive coefficient may be $\lambda_{100}$ or $\lambda_{111}$ or even $\lambda^{\gamma,2}$ or $\lambda^{\epsilon,2}$. These measurement results are shown in the sample calibration table.

The Third Embodiment

The present invention for use in creating the calibration table in the case of calibrating macroscopic external magnetostrictive coefficient measurement device at low temperature will be explained below with reference to other embodiments.

In this third embodiment, the standard calibration sample is, for example, a single crystal sample of iron. This single crystal sample of iron presents a property of (t$_i$, $\lambda^{Fe}$(t$_i$)) at low temperatures. Here, $\lambda^{Fe}$(t$_i$) is a crystallographical magnetostrictive coefficient at temperature T=t$_i$ (i=1,2,3. . . ) measured by observing the change of the lattice spacing by X-ray diffraction method according to the present invention.

The macroscopic magnetostriction measurement device, for example strain gauge, is attached to the standard sample for calibration in advance, at room temperature.

This standard sample for calibration attached to the strain gauge is placed under the same condition as the environment in which the magnetostriction property was evaluated by observing the change of the lattice spacing by X-ray diffraction method. Here, the electric resistance value of the strain gauge at the demagnetized state $r_0^{Fe}$ and at the saturation magnetization state $r_{SM}^{Fe}$ are measured along with the set temperature condition T=t$_i$.

Figure 6:
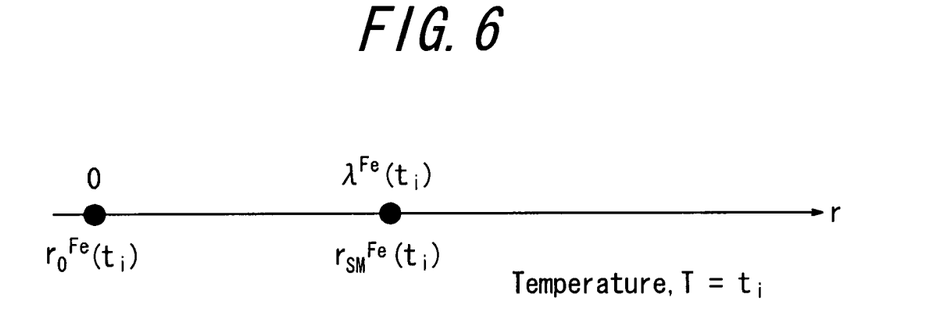
FIG. 6 is an explanatory diagram showing with a number line, the relation of the output electric resistance value of strain gauge and the calibration value at temperature T=$t_i$, for an iron sample.

FIG. 6 shows the relation between the actual measurement of the strain gauge output electric resistant value of iron, and the calibration value of the magnetostrictive coefficient at temperature T=t$_i$ on a number line, so as to explain the principle of the calibration method and usage of the strain gauge. More specifically the axis r of FIG. 6 shows the output resistance of the strain gauge, the output resistance value is noted at the lower part of axis r, and the corresponding magnetostrictive coefficient is noted at its upper part. Indicated on the left of the drawing is the output resistance of the strain gauge $r_0^{Fe}$(t$_i$) against the iron sample at magnetization 0, in which the magnetostrictive coefficient is 0. On the other hand, indicated at the facility of the drawing is the output resistance of the strain gauge $r_{SM}^{Fe}$(t$_i$) against the iron sample at saturation magnetization, in which the magnetostrictive coefficient is $\lambda^{Fe}$(t$_i$) according to the calibration table of the sample.

In this way, these two kinds of physical quantities are added to a calibration table for the sample consisting of two kinds of physical quantities to create a calibration table for a given strain gauge consisting of a total of four physical quantities (t$_i$, $\lambda^{Fe}$(t$_i$), $r_0^{Fe}$(t$_i$), $r_{SM}^{Fe}$(t$_i$)). The four physical quantities mentioned above are, temperature, magnetostrictive coefficient, the output resistance of strain gauge at the demagnetized state, and the output resistance of strain gauge at saturation magnetization. It is preferable that the set temperature is appropriately subdivided. The magnetostrictive coefficient may be $\lambda_{100}$ or $\lambda_{111}$ or even $\lambda^{\gamma,2}$ or $\lambda^{\epsilon,2}$.

The Fourth Embodiment

The present invention for use in creating the calibration table in the case of calibrating macroscopic magnetostrictive coefficient measurement device at low temperature will be explained further with reference to other embodiments.

In this fourth embodiment, the case in which the magnetostrictive coefficient $\lambda^X(t_i)$ of a product of given element at temperature T=$t_i$ is measured by attaching the strain gauge having the above mentioned calibration table.

For the calibration of magnetostrictive coefficient measurement device at low temperature volumes, the deviation from the condition set at room temperature must be corrected, for example, the heat expansion coefficient affected by thermal contraction must be taken into account. Therefore, for the calibration of strain gauge at low temperature, the preparation of at least two standard samples for calibration where each of the samples are made of different elements and each has known calibration values $(t_i, \lambda(t_i))$, are necessary. For example, a ferromagnetic single crystal standard sample of iron, or of other elements, such as cobalt or nickel is candidates. Alloys or oxides containing these elements may also be possible.

For example, here, two pairs of calibration values consisting of four physical quantities $(t_i, \lambda^{Fe}, r_0^{Fe}, r_{SM}^{Fe})$ (See hereinafter described FIG. 7(b), L1 for reference) and $(t_i, \lambda^{Ni}, r_0^{Ni}, r_{SM}^{Ni})$ (See hereinafter described FIG. 7(b), L1 for reference) are utilized, where the magnetostrictive coefficients in the orientation of the easy magnetization at every temperature are known for the iron(Fe) and nickel(Ni) single crystal standard samples for calibration obtained at a certain temperature. Here, the magnetostrictive coefficients $\lambda^{Fe}$ and $\lambda^{Ni}$ may be $\lambda_{100}$ or $\lambda_{111}$ or even $\lambda^{\gamma,2}$ or $\lambda^{\epsilon,2}$.

The strain gauge is attached in advance at room temperature to the object to be measured X, the subject of evaluation of which the magnetostrictive coefficient is unknown. For example, the object to be measured X may include all products in general which the conventional strain gauge has measured, for example candidate samples for the second standard sample.

Figure 7:
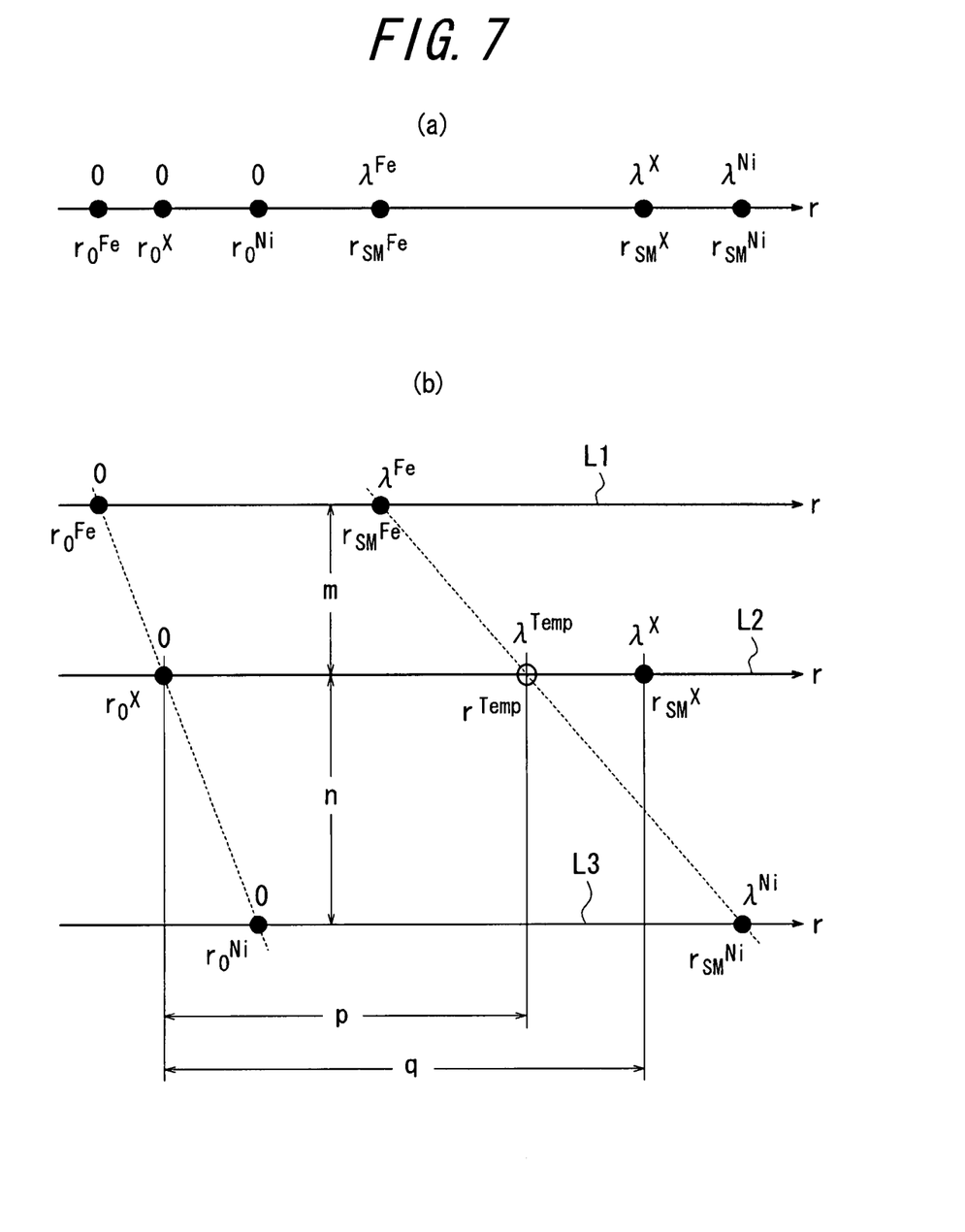

Here, FIGS. 7(a), 7(b) show the relation between the actual measurement of the strain gauge output resistant value of iron, and the magnetostrictive coefficient at a certain temperature $t_i$ on a number line of which the output electric resistance is represented by axis r, so as to explain the principle of the calibration method and usage of the strain gauge. The output electric resistance value is noted at the lower part of axis r, and the corresponding magnetostrictive coefficient is noted at its upper part. FIG. 7(a) is a compilation of the output electric resistance value of the strain gauge on the calibration table, the known value of magnetostrictive coefficient, and all the values related to object X to be measured at temperature $t_i$. On the other hand, FIG. 7(b) is an explanatory diagram showing the part (L1) on iron of the calibration table mentioned in FIG. 7(a), and the part (L2) relating to the idea for obtaining the magnetostrictive coefficient of the object X to be measured, and the part (L3) on nickel of the calibration table mentioned in FIG. 7(a).

Given that the actually measured resistance value at the demagnetized state and the saturation magnetization state at a certain temperature $t_i$. were $r_0^X(t_i)$ and $r_{SM}^X(t_i)$, respectively (See FIGS. 7(a), 7(b), L2 for reference), the magnetostrictive coefficient $\lambda^X(t_i)$ of this product can be obtained in the following way. First, for the correction relating to the heat expansion coefficient, the fraction to the thermal expansion coefficient of the actual measurement value of iron and nickel

[No. 9]
$$m = r_0^X - r_0^{Fe} \tag{9}$$

[No. 10]
$$n = r_0^{Ni} - r_0^X \tag{10}$$

are taken into account. $r_0^X$ is the interpolating point which divides $r_0^{Fe}$ and $r_0^{Ni}$ to m to n (i.e. L2 of FIG. 7(b)) is indicated on the point where L1 and L2 are divided to m to n). Here, m is the proportional constant of $r_0^{Ni}$ to $r_0^{Fe}$ in $r_0^X$, and n is the proportional constant of $r_0^{Fe}$ to $r_0^{Ni}$ in $r_0^X$.

From the ratio calculations weighted with these proportions (L1 to L3 of FIG. 7(b)), the provisional value of the magnetostrictive coefficient $\lambda^{Temp}$ (See FIG. 7(b) facility of L2 for reference) when the output electric resistance of the strain gauge of object X to be measured presents, for example $r^{Temp}$ (See FIG. 7(b) facility of L2 for reference) can be obtained in the following way, by utilizing the calibration result of iron and nickel (See FIG. 7(b) L1, L3 for reference).

[No. 11]
$$r^{Temp} = \frac{mr_{SM}^{Ni} + nr_{SM}^{Fe}}{m+n} \tag{11}$$

[No. 12]
$$\lambda^{Temp} = \frac{m\lambda^{Ni} + n\lambda^{Fe}}{m+n} \tag{12}$$

Next, with the difference of the provisional value of the output resistance of the strain gauge $r^{Temp}$ (See FIG. 7(b) facility of L2 for reference) and the actual measurement value $r_0^X$ (See FIG. 7(b) left side of L2 for reference), and the actual measurement value $r_{SM}^X$,

[No. 13]
$$p = r^{Temp} - r_0^X \tag{13}$$

[No. 14]
$$q = r_{SM}^X - r_0^X \tag{14}$$

the ratio calculation is done again (See FIG. 7(b) lower part of L3 for reference) to obtain the magnetostrictive coefficient of interest $\lambda^X$ (See FIG. 7(b) right side of L2 for reference) related to object X to be measured, by extrapolation (See FIG. 7(b) right side of L2 for reference).

[No. 15]
$$\lambda^X = \frac{q}{p}\lambda^{Temp} \tag{15}$$

If object X to be measured is the second calibration sample, the physical quantities to be listed in the calibration table for the second calibration sample are of two kinds; $(t_i, \lambda^X(t_i))$. Here, temperature T=$t_i$ is the set temperature, and $\lambda^X(t_i)$ is the value of magnetostriction corresponding to the electric resistance of a certain strain gauge. It is preferable that the set temperature is appropriately subdivided.

The Fifth Embodiment

Figure 8:
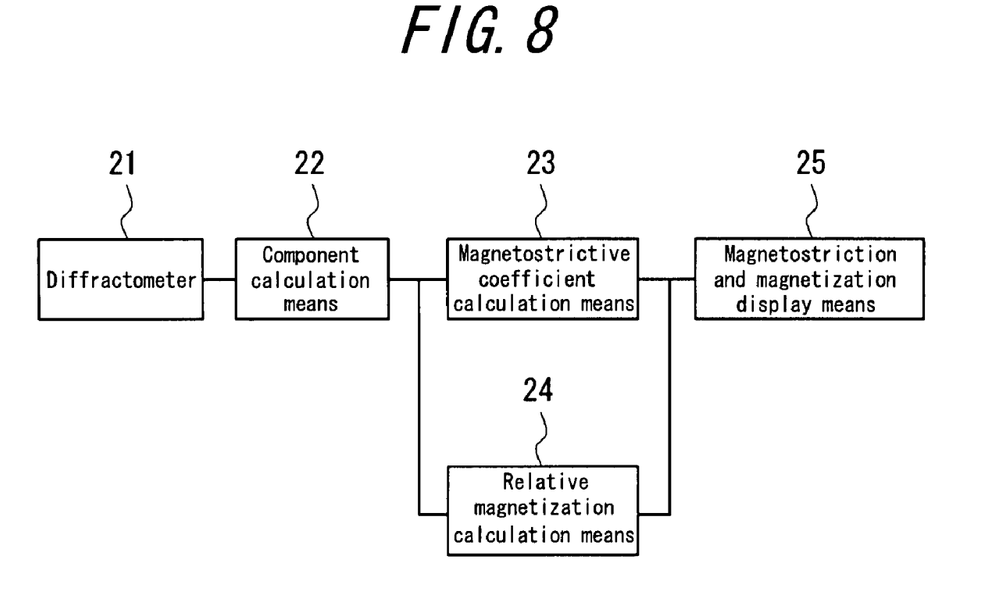
FIG. 8 is a block diagram showing the constitution of an embodiment of the device for the simultaneous measurement of the magnetostriction and the magnetization with the measurement method according to the present invention.

FIG. 8 is a block diagram showing the constitution of an embodiment of the device for the simultaneous measurement of magnetostriction and magnetization utilizing the method of measurement according to the present invention. The present device in this fifth embodiment, is a device which measures the magnetostriction and magnetization at the coextensive volumes of the sample simultaneously and is able to provide a device for the simultaneous measurement of magnetostriction, characterized in that it has a goniometer 21 which measures the relative diffraction intensity change δ of diffraction intensity at ascending magnetic field and descending magnetic field respectively in said volumes of said sample, a component calculation means 22 which obtains symmetry component $\delta_A$ and asymmetry component $\delta_B$ to the magnetic field H from the relative diffraction intensity change $\delta$ at the above mentioned ascending magnetic field and descending magnetic field, a magnetostrictive coefficient calculation means 23 which obtains magnetostrictive coefficient $\lambda_{100}$ of said volumes of said sample based on said symmetry component $\delta_A$, and a relative magnetization calculation means 24 which obtains relative magnetization $M/M_s$ of said volumes of said sample based on the value $R'_a$ obtained by recomposing said symmetry component $\delta_A$ and asymmetry component $\delta_B$, and a magnetostriction and magnetization display means 25 which displays the said obtained magnetostrictive coefficient and relative magnetization on the screen simultaneously.

This goniometer 21 of the fifth embodiment, may be constituted for example, by using the goniometer 8 shown in FIG. 5, and the component calculation means 22, the magnetostrictive coefficient calculation means 23, the relative magnetization calculation means 24, and the magnetostriction and magnetization display means 25 of the present embodiment may be constituted by implementing some software which make a regular personal computer to carry out the functions of each of these means, and the magnetostriction and magnetization display means 25 enables the display of the obtained magnetostrictive coefficient and relative magnetization on the screen simultaneously.

INDUSTRIAL APPLICABILITY

In this way, according to the present invention, the measurement of the magnetostriction and the magnetization at exact coextensive specimen volumes is possible, the adaptation of the crystallographical magnetostrictive coefficient, obtained by the observation of the change of the lattice spacing by the method according to the present invention, to the macroscopic external magnetostrictive coefficient measuring device is enabled, and a magnetic substance such as a standard sample for calibration evaluated using the methods of the present invention, devises such as sensors calibrated using these standard samples for calibration evaluated using the methods of the present invention, and a device for simultaneous measurements of the magnetostriction and the magnetization using the above measurement methods can be provided.

The invention claimed is:

1. A method for simultaneous measurement of magnetostriction and magnetization of a sample at coextensive volumes of the sample, comprising the steps of:
measuring a relative diffraction intensity change ($\delta$) at an ascending magnetic field and at a descending magnetic field respectively in the coextensive volumes of the sample to obtain an asymmetry component ($\delta_A$) and a symmetry component ($\delta_S$) of a magnetic field (H) from the relative diffraction intensity change ($\delta$) at the coextensive volumes of the sample;
obtaining a magnetostrictive coefficient ($\lambda_{100}$) at the coextensive volumes of the sample based on the symmetry component ($\delta_S$);
obtaining a relative magnetization ($M/M_s$) at the coextensive volumes of the sample based on a value ($R'_a$) obtained by recomposing the asymmetry component ($\delta_A$) and the symmetry component ($\delta_S$); and
displaying the magnetostriction and magnetization at the coextensive volumes of the sample.

2. The method for the simultaneous measurement of the magnetostriction and the magnetization of the sample described in claim 1, wherein the relative diffraction intensity change ($\delta$) of the magnetic field is measured by X-ray magnetic diffraction.

3. A method for obtaining a standard calibration sample, the method comprising simultaneously measuring magnetostriction and magnetization of the standard calibration sample at coextensive volumes of the sample according to the method of claim 1.

4. A method for obtaining a standard calibration sample, the method comprising simultaneously measuring magnetostriction and magnetization of the standard calibration sample at coextensive volumes of the sample according to the method of claim 2.

5. A standard calibration sample for magnetostriction measurement devices obtained according to the method described in claim 3.

6. A standard calibration sample for magnetostriction measurement devices obtained according to the method described in claim 4.

7. A device for measuring the magnetostriction calibrated using standard samples for calibration as described in claim 5.

8. A device for measuring the magnetostriction calibrated using standard samples for calibration as described in claim 6.

9. A device for simultaneous measurement of magnetostriction and magnetization of a sample at coextensive volumes of the sample, comprising:
a diffractometer which measures a relative diffraction intensity change ($\delta$) at an ascending magnetic field and at a descending magnetic field respectively in a magnetic field (H) at the coextensive volumes of the sample;
a component calculation means which obtains an asymmetry component ($\delta_A$) and a symmetry component ($\delta_S$) of the magnetic field (H) from the relative diffraction intensity change ($\delta$) at the ascending magnetic field and the descending magnetic field;
a magnetostrictive coefficient calculation means which obtains a magnetostrictive coefficient ($\lambda_{100}$) of the coextensive volumes of the sample based on the asymmetry component ($\delta_S$);
a relative magnetization calculation means which obtains a relative magnetization ($M/M_s$) at the coextensive volumes of the sample based on a value ($R'_a$) obtained by recomposing the asymmetry component ($\delta_A$) and the symmetry component ($\delta_S$); and
a magnetostriction and magnetization display means which displays the obtained magnetostrictive coefficient and relative magnetization on a screen.

* * * * *